United States Patent
Scampini

(10) Patent No.: US 7,666,358 B2
(45) Date of Patent: Feb. 23, 2010

(54) CELL BLOCK CASSETTE DEVICE

(75) Inventor: Steven A. Scampini, Groton, MA (US)

(73) Assignee: Cytyc Corporation, Marlborough, MA (US)

( * ) Notice: Subject to any disclaimer, the term of this patent is extended or adjusted under 35 U.S.C. 154(b) by 510 days.

(21) Appl. No.: 11/551,623

(22) Filed: Oct. 20, 2006

(65) Prior Publication Data

US 2008/0097285 A1    Apr. 24, 2008

(51) Int. Cl.
*B01L 3/00*    (2006.01)
(52) U.S. Cl. .............................. 422/99; 422/63; 422/64; 422/65; 422/67; 422/100; 422/110; 436/174; 436/180
(58) Field of Classification Search .................. 436/174, 436/180; 422/99–100, 61, 102, 58, 63–65, 422/67, 110
See application file for complete search history.

(56) References Cited

U.S. PATENT DOCUMENTS

| | | | | |
|---|---|---|---|---|
| 3,698,822 | A | * | 10/1972 | Polanyi ...................... 356/246 |
| 4,007,010 | A | * | 2/1977 | Woodbridge, III ........... 422/50 |
| 4,595,549 | A | | 6/1986 | Inouye et al. |
| 4,801,553 | A | * | 1/1989 | Owen et al. .................. 436/174 |
| 5,354,370 | A | * | 10/1994 | Schmehl ...................... 118/50 |
| 5,614,376 | A | | 3/1997 | Copley et al. |
| 5,843,700 | A | | 12/1998 | Kerrod et al. |
| 6,489,171 | B1 | | 12/2002 | Aghassi et al. |
| 6,913,921 | B2 | | 7/2005 | Fischer |
| 2004/0121456 | A1 | | 6/2004 | Fischer |
| 2005/0186114 | A1 | | 8/2005 | Reinhardt et al. |

FOREIGN PATENT DOCUMENTS

| | | |
|---|---|---|
| EP | 0826955 | 3/1998 |
| WO | 2007137272 | 11/2007 |

OTHER PUBLICATIONS

PCT International Search Report for PCT/US2007/079963, Applicant CYTYC Corp., Forms PCT/ISA/210 and 220, dated Jan. 30, 2008 (6 pages).
PCT Written Opinion of the International Search Authority for PCT/US2007/079963, Applicant CYTYC Corp., Form PCT/ISA/237, dated Jan. 30, 2008 (7 pages).

* cited by examiner

*Primary Examiner*—Jill Warden
*Assistant Examiner*—Sally A Sakelaris
(74) *Attorney, Agent, or Firm*—Vista IP Law Group LLP

(57) ABSTRACT

A tissue cassette assembly includes a housing having a recess formed therein, and a compressible reservoir disposed partially or wholly inside of, or otherwise attached in fluid communication with, the housing recess, the compressible reservoir containing a tissue embedding material. The tissue cassette further includes a port disposed in the housing, the port in fluid communication with the compressible reservoir at one end and terminating in a sample cavity at another end. During operation, the compressible reservoir is compressed or squeezed to release the tissue embedding material into the sample cavity containing the biological sample.

21 Claims, 2 Drawing Sheets

CELL BLOCK CASSETTE DEVICE

FIELD OF THE INVENTION

The present invention relates to devices for embedding biological samples in a solid or semi-solid medium.

BACKGROUND

A technique, commonly referred to as a cell block preparation, has been used for preparing embedded biological samples for further analysis. The cell block procedure immobilizes cells or small tissue fragments in a solid or semi-solid support, typically paraffin or wax. Thin sections of the cell block are then cut with a microtome and the sections mounted onto a microscope slide for examination. The resulting sections from the cell block display diagnostic information in a manner that complements direct deposition techniques.

The cell block preparation method requires that the cell fragments be "embedded" in a solid or semi-solid medium, most commonly paraffin wax. "Embedding" typically requires the following steps: (1) all water molecules must be removed from the cells, typically by alcohol (water is miscible with alcohol); (2) all alcohol must then be removed, as well as all fatty substances, and replaced typically by xylene (xylene is miscible with alcohol but not water); (3) the xylene must be removed and replaced with wax (wax is miscible with xylene but not with most alcohols or water); and (4) the cells in molten wax must then be manually organized and hardened on the underside of a tissue cassette so that a section of the wax block with the embedded tissue can be cut using a microtome.

U.S. Pat. No. 6,913,921 discloses methods and apparatuses for preparing embedded samples. The '921 patent, which is incorporated by reference as if set forth fully herein, discloses placing a biological sample on a filter, washing it with alcohol and xylene, and embedding the sample in paraffin wax. A drawback of the disclosed method is the use of a bulk paraffin reservoir, which requires special heating and pumping systems.

SUMMARY OF THE INVENTION

Disclosed herein is a tissue cassette assembly comprising a reservoir; a sample cavity; and at least one delivery passage in communication with the reservoir and the sample cavity. Also disclosed herein is a reservoir adapted to fit wholly or partially within, or otherwise connect to, a tissue cassette assembly, the reservoir being in fluid communication with the sample cavity. Furthermore, disclosed herein is a method of embedding biological material in tissue embedding material. The method includes the steps of: obtaining a tissue cassette assembly comprising a sample cavity and a reservoir, where the reservoir contains tissue embedding material, and where the reservoir is in fluid communication with the sample cavity through a passageway or port; placing the biological material within the sample cavity; squeezing the reservoir, thereby releasing the tissue embedding material from the reservoir into the sample cavity through the passageway, thereby embedding the biological material within the tissue embedding material.

In one embodiment, the tissue cassette assembly includes a housing or body that includes a recess for receiving and holding a compressible reservoir. The compressible reservoir is configured to contain a tissue embedding material such as, for instance, paraffin. The compressible reservoir is fluidly coupled to a sample cavity that is disposed inside the housing. The compressible reservoir may be fluidly coupled to the sample cavity using one or more channels or tubes. In addition, the tissue cassette assembly may include an optional valve interposed between the compressible reservoir and the sample cavity. The valve may open or permit the passage of tissue embedding material after a sufficient threshold amount of compressive force is applied to the compressible reservoir. The tissue cassette assembly may have multiple reservoirs (e.g., upper and lower) located in separate recesses of the housing. The compressible reservoir may be permanently attached or otherwise secured to the tissue cassette assembly. Alternatively, the compressible reservoir may be attached or inserted into (whether manually or automatically) the housing body (e.g., for example, inserted after manufacture).

In another embodiment, a tissue cassette assembly includes a housing having at least one recess therein, and a compressible reservoir disposed inside the at least one recess of the housing, the compressible reservoir configured to contain tissue embedding material. The tissue cassette further includes at least one port disposed in the housing, the at least one port being in fluid communication with the compressible reservoir at one end and terminating in a sample cavity at another end.

In still another embodiment, a method of embedding biological material in tissue embedding material includes providing a tissue cassette assembly of the type described above. Biological material is then placed inside the sample cavity. The reservoir is then compressed (e.g., squeezed) to release the tissue embedding material from the compressible reservoir into the sample cavity so as to embed the biological material within the tissue embedding material. In one aspect, the biological material is placed on a piece of filter paper or similar porous media that is fixedly secured inside the sample cavity. For example, the filter paper may rest overtop a metallic plate having a plurality of apertures or holes therein.

In still another embodiment, a reservoir for containing a tissue embedding material includes a compressible container having at least one opening, the compressible container configured to contain a volume of tissue embedding material therein, the compressible container being further configured to fluidly couple with at least one port in a tissue cassette assembly, the at least one port being in fluid communication with a sample cavity disposed within the tissue cassette assembly.

In yet another embodiment of the invention, a tissue cassette assembly includes a housing having at least one recess therein, the at least one recess containing a tissue embedding material. A moveable piston is disposed inside the at least one recess of the housing, the moveable piston configured to apply pressure to the tissue embedding material in the recess. The tissue cassette further includes at least one port disposed in the housing, the at least one port being in fluid communication with the tissue embedding material in the recess at one end and terminating in a sample cavity at another end.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Embodiments of the present invention are described below. It is, however, expressly noted that the present invention is not limited to these embodiments, which are provided by way of example and not limitation. Aspects of the present invention are directed to a cell block cassette assembly having a reservoir or a pouch that can contain a liquid or semi-liquid substance, such as alcohol, xylene, or a tissue embedding material, such as liquefied wax, paraffin, paraffin with additives, plastics, and the like. In some embodiments, the tissue embedding material is paraffin. Once the pouch or reservoir is squeezed, either manually or by an instrument, the contents of the pouch or reservoir is emptied into a sample cavity, which contain a biological sample, such as cells or tissue. The use of the pouch or reservoir embedded within the cell block cassette removes the need for an external reagent flask. Some of the benefits of the present invention include the convenience of not needing to load bulk wax and virtually eliminating the problems of contamination of the wax during handling and the possibility of using waxes that are not qualified to work in the apparatus. In addition, the cell block cassette having the reservoir may optionally be disposable. In these embodiments, maintenance of the wax pumping system and possible problems with buildup and clogs is virtually eliminated.

Figure 1A:
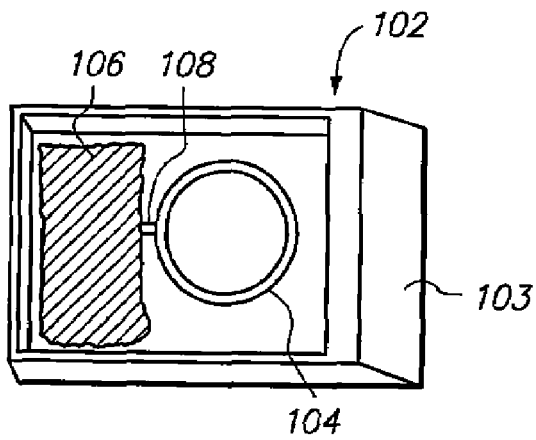
FIG. 1A depicts a top view of an embodiment of a cell block device having one passageway or port coupling the reservoir and the sample cavity.
Figure 3A:
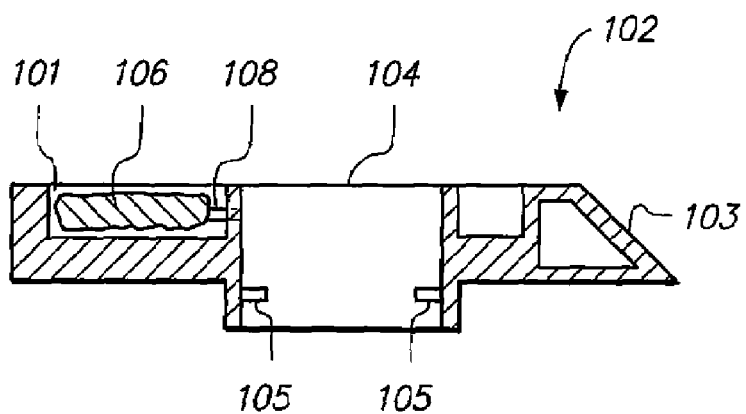
FIG. 3A depicts a cross-sectional view of an embodiment of a cell block device according to one embodiment, wherein a reservoir is located at the top side of the cell block.
Figure 3B:
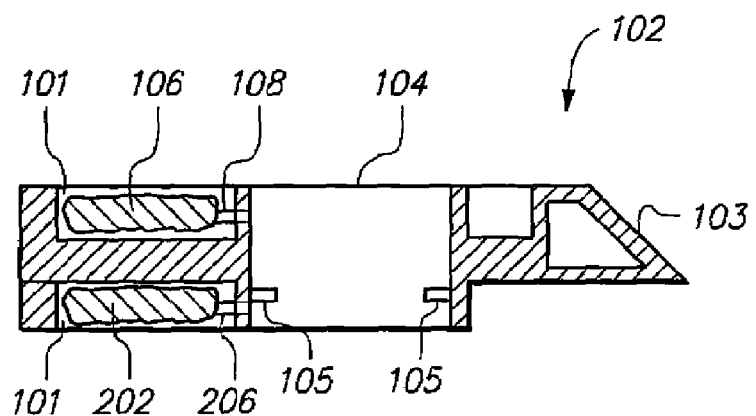
FIG. 3B depicts a cross-sectional view of an embodiment of a cell block device, wherein a first reservoir is located at the top side of the cell block and a second reservoir is located at the bottom side of the cell block.

FIG. 1A shows an embodiment of the tissue cassette 102. The tissue cassette 102 generally includes a housing or body portion 103 that includes the various working features of the device. The housing or body portion 103 may be formed, at least in part, from a polymer or plastic material. The housing or body portion 103 may be formed as a single unit. Alternatively, the housing or body portion 103 may be formed from multiple sub-units that are then subsequently bonded or affixed to form a unitary construction such as that illustrated in FIG. 1A. The tissue cassette 102 includes a sample cavity 104, which is adapted to receive cells, tissues, or other biological samples to be embedded in the solid support medium. The sample cavity 104 may be milled or drilled out of the housing or body portion 103. As seen in FIGS. 3A, 3B, and 3C, the sample cavity 104 may have support member 105 disposed about the periphery of the sample cavity 104. For example, the support member 105 may be formed as a ring or series or projections that extend radially inward from the sample cavity 104. The support member 105 (or plurality of members 105) may be used to rest a porous member such as a plate or even filter paper during the embedding process. For example, a metal plate (not shown) having a plurality of holes may be inserted into the sample cavity 104. Filter paper or other porous media may then be positioned over the metal plate to create the thin layer of cells or biological tissue needed for the embedding process.

Still referring to FIG. 1A, the sample cavity 104 is cylindrical in shape. However, in other embodiments, the sample cavity 104 can have other shapes including, for example, cross-sectional shapes of a square, triangle, polygon (e.g., pentagon, hexagon, heptagon, octagon, etc.), oval, or the like. The tissue cassette 102 also includes a pouch or reservoir 106 that is disposed inside a recess 101 that is located in the housing 103. In alternate embodiments, the reservoir 106 is attached to the tissue cassette 102, but is not within a recess located in the housing 103. The reservoir 106 is configured as a compressible or flexible container that holds a tissue embedding material, such as wax, paraffin, paraffin with additives, plastics, and the like. The reservoir 106 is constructed from material that is resistant to degradation due to exposure to certain chemicals, such as paraffin, plastics, other waxes, and solvents, such as water, alcohols, and xylene. The construction material for the reservoir 106 is also resistant to degradation due to exposure to the temperature required to melt the tissue embedding material and pressure required to remove the tissue embedding material from the reservoir 106. The reservoir 106 may be constructed from flexible plastic or other polymer material, metal foil, polyester, fluorocarbon polymer, vinyl, and rubber. The reservoir 106 has sufficient strength such that any fluid contained therein will not leak or burst out in response to an applied pressure (except for that portion in communication with the sample cavity 104 described in detail below).

In certain embodiments, the reservoir 106 may be permanently affixed to the tissue cassette 102. In other embodiments, the reservoir 106 can be removed and replaced by another reservoir 106. In certain embodiments, the reservoir 106 in filled at a central location, such as a factory or a manufacturing facility, affixed to the tissue cassette 102, and shipped as such. In other embodiments, the reservoir 106 is empty when shipped and is filled by the end user. In further embodiments, the reservoir 106 is refillable by the end user.

Figure 1B:
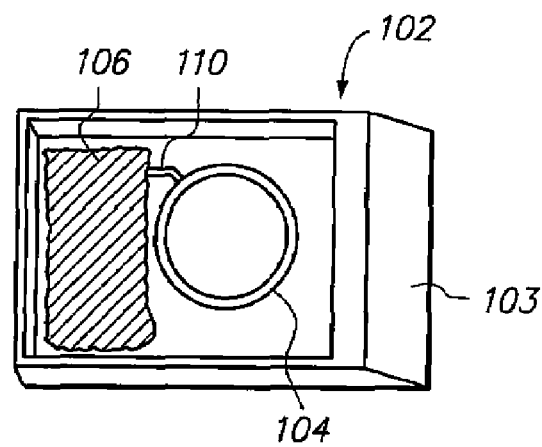
FIG. 1B depicts a top view of another embodiment of a cell block device wherein there is a single passageway or port located at the side of the reservoir between the reservoir and the sample cavity (e.g., cell block chamber).
Figure 1C:
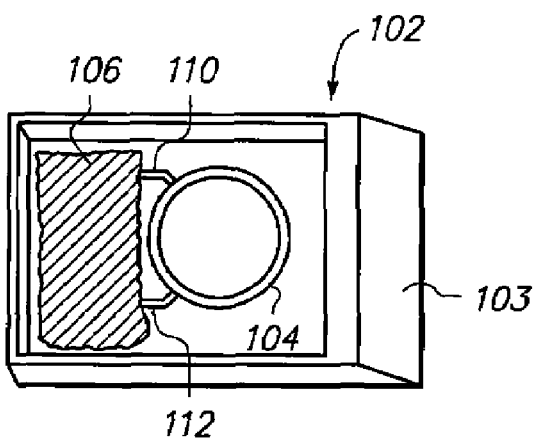
FIG. 1C depicts a top view of another embodiment of a cell block device wherein there are two passageways or ports connecting the reservoir and the sample cavity.

As shown in FIG. 1A, the reservoir 106 is in fluid communication with the sample cavity 104 through a passageway or port 108. As seen in FIG. 1A, the passageway 108 is located at the central region of the reservoir 106. In another embodiment, shown in FIG. 1B, the passage 110 is located at one side of the reservoir 106. This embodiment is particularly useful if the contents of the reservoir 106 are emptied through the action of a roller, which rolls from one side to another in a direction generally perpendicular to the long axis of the tissue cassette 102. In yet another embodiment, shown in FIG. 1C, two passages, 110 and 112, are located at opposite sides of the reservoir 106 and connect the reservoir 106 to the sample cavity 104. This embodiment is particularly useful for a more even distribution of the tissue embedding material within the sample cavity 104 and for a more rapid dispensing of the tissue embedding material. FIG. 3A shows a cross-section of the embodiment shown in FIG. 1A.

Figure 2:
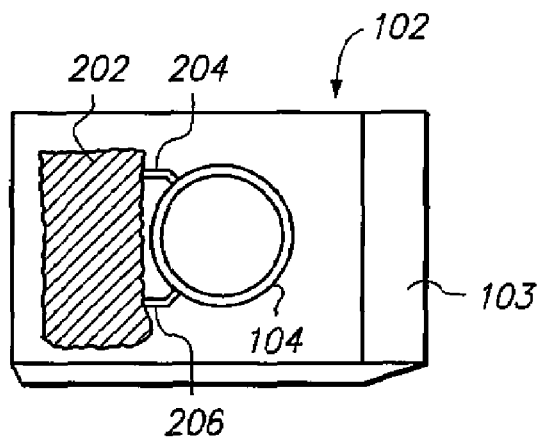
FIG. 2 depicts a bottom view of a cell block device having multiple (upper and lower) reservoirs. Only one such reservoir can be seen in FIG. 2.

In some embodiments, as shown in FIGS. 2 and 3, in addition to having a reservoir 106 at its top side, the tissue cassette 102 has another reservoir 202 at its bottom side. The top and bottom reservoirs 106, 202 may be located in separate recesses 101, 101' formed in the tissue cassette 102. The bottom or lower reservoir 202 is in fluid communication with the sample cavity 104 through at least one passageway 206. FIG. 2 shows one embodiment in which two passages, 204 and 206, connect the reservoir 202 with the sample cavity 104. FIG. 3B shows a cross-sectional view of the embodiment shown in FIG. 2.

In some embodiments, the passageways 108, 110, 112, 204, and 206, each is independently a channel molded in the plastic body of tissue cassette 102. For example, the tissue cassette 102 may be formed from two halves—each half containing a partial channel that, when combined, form the fluid passageways. In other embodiments, the passages 108, 110, 112, 204, and 206, each is independently a tube that connects the reservoir 106 or 202 with the sample cavity 104. When the passages are a tube, the tube is constructed from material that is resistant to degradation due to exposure to certain chemicals, such as paraffin, other waxes, and solvents, such as water, alcohols, and xylene.

Figure 4:
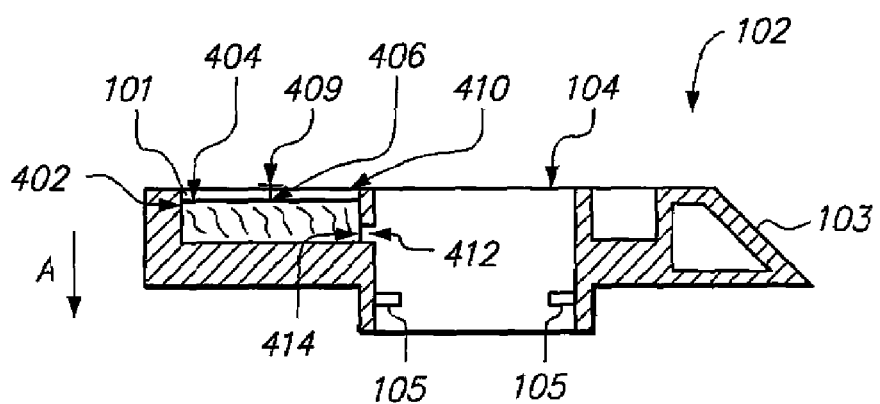
FIG. 4 depicts a cross-sectional view of an embodiment of a cell block, wherein the reservoir includes a moveable piston.

FIG. 4 shows another embodiment of the reservoir 402 in the tissue cassette 102. The reservoir 402 comprises a piston assembly 403 that is located in a recess 101 of the tissue cassette 102. The piston assembly 403 comprises a moveable piston 404 (moveable in the direction of arrow A in FIG. 4). While FIG. 4 illustrates the piston 404 as occupying the top edge of the reservoir 402, in other embodiments, the piston 404 occupies one of the sides of the reservoir 402, while in still other embodiments, the piston 404 is at the bottom of the reservoir 402. The piston assembly 403 further comprises a shaft 406, which connects the piston 404 to a boss 408.

In some embodiments, the side of the reservoir containing the boss 408, e.g., the top side 410 in FIG. 4, is flexible, thus allowing the boss 408 greater freedom of movement. In other embodiments, the shaft 406 is of such length that when the boss 408 is depressed, the piston 404 moves through substantially all of the reservoir 402.

When the boss 408 is depressed, the piston 404 moves down (in direction of arrow A) and pushes the contents of the reservoir 402, e.g., paraffin or other tissue embedding material, into the sample cavity 104 through a channel 412. In some embodiments, an optional valve 414 separates the reservoir 402 from the sample cavity 104. When the boss 408 is depressed, the pressure of the contents of the reservoir 402 causes the valve 414 to open and allow for the contents of the reservoir 402 to move to the sample cavity 104. For example, the valve 414 may open or even break upon application of compressive or squeezing force that is above a certain threshold level.

In another aspect, the reservoir 106, 202 is adapted to fit within a tissue cassette 102, where the reservoir 106, 202 is adapted to contain tissue embedding material. In some embodiments, the tissue embedding material is paraffin. The reservoir 106, 202 may contain tissue embedding material in an amount sufficient to embed a biological sample within the sample cavity 104 with tissue embedding material. In certain embodiments, the reservoir 106, 202 is constructed from material resistant to degradation due to exposure to a condition selected from the group consisting of contact with the tissue embedding material, contact with solvents, high temperature required to melt the tissue embedding material, and pressure required to remove the tissue embedding material from the reservoir. The material may include, for example, flexible plastic, metal foil, polyester, fluorocarbon polymer, vinyl, and rubber.

A method of embedding biological material in tissue embedding material may include the steps of obtaining a tissue cassette assembly comprising a sample cavity 104 and a reservoir 106, 202, where the reservoir 106, 202 contains the tissue embedding material, and where the reservoir 106, 202 is in fluid communication with the sample cavity 104 through a delivery passageway 108, 110, 112, 204, 206. The biological material is placed within the sample cavity 104 and the reservoir 106, 202 is compressed or depressed so as to release the tissue embedding material from the reservoir 106, 202 into the sample cavity 104 through the passageway 108, 110, 112, 204, 206, thereby embedding the biological material within the tissue embedding material.

In certain embodiments, the reservoir 106, 202 contains tissue embedding material in an amount sufficient to at least partially fill the sample cavity 104 with the tissue embedding material. In further embodiments, the reservoir 106, 202 is constructed from material resistant to degradation due to exposure to the tissue embedding material, solvents, high temperatures required to melt the tissue embedding material, and pressure required to remove the tissue embedding material from the reservoir. In some embodiments, the reservoir 106, 202 is formed from a material such as, for instance, flexible plastic, metal foil, polyester, fluorocarbon polymer, vinyl, and rubber.

The reservoir 106, 202 may be permanently affixed to the tissue cassette 102. In an alternative embodiment, the reservoir 106, 202 is replaceable. In certain embodiments, the reservoir 106, 202 is refillable. As described herein, the delivery passage way 108, 110, 112, 204, 206 is a channel constructed within the tissue cassette 102. In other embodiments, the delivery passage is a tube embedded within the tissue cassette assembly. In some of these embodiments, the tube is constructed from material resistant to degradation. For example, the tube may be formed from a material that resists degradation in response to exposure to the tissue embedding material, exposure to solvents, and exposure to elevated temperatures and pressures.

The biological material used in connection with the tissue cassette 102 may include a collection of cells or cellular bodies. In certain embodiments, the biological material may also include a tissue sample. For example, the tissue sample may be taken from a certain organ or body tissue for subsequent imaging and analysis.

As explained herein, the tissue embedding material is contained within a reservoir 106, 202. The tissue embedding material may be stored within the reservoir 106, 202 in a solid or semi-solid state. In this regard, the tissue embedding material may need to be heated to partially or fully melt the tissue embedding material into the liquid or semi-liquid state. Once the tissue embedding material is in a liquid or even semi-liquid state, the reservoir 106, 202 can be compressed (e.g., squeezed) to transfer the tissue embedding material to the one or more delivery passageways 108, 110, 112, 204, 206 and into the sample cavity 104.

In some embodiments, the method disclosed herein further comprises placing a porous plate on the support member 105 (or plurality of members 105). For example, a metal plate (not shown) having a plurality of holes may be inserted into the sample cavity 104 and held in place via the one or more support members 105. A piece of filter paper or other porous media may then be positioned over the metal plate to create the thin layer of cells or biological tissue needed for the embedding process. Once a layer of biological material has been deposited on the filter paper (or other porous media), the reservoir 106, 202 may be squeezed to deposit the embedding material on top of the biological material.

If a tissue cassette 102 of the type disclosed in FIG. 3B is used, the method may further include the step of squeezing a second reservoir (e.g., 202), thereby releasing the tissue embedding material from the second reservoir 202 into the sample cavity 104 through a passageway 206, where the tissue embedding material from the second reservoir 202 is released below the filter paper (or other porous media).

According to one aspect of the method of embedding a biological sample within an embedding media, the method disclosed herein further comprises treating the biological material sequentially with an alcohol and xylene prior to the squeezing step.

The invention may be embodied in other specific forms besides and beyond those described herein. The foregoing embodiments are therefore to be considered in all respects illustrative rather than limiting, and the scope of the invention is defined only by the appended claims and their equivalents, rather than by the foregoing description.

What is claimed is:

1. A tissue cassette assembly, comprising:
   a housing;
   a compressible reservoir disposed in and attached to the housing, the compressible reservoir containing a tissue embedding material;
   a passageway disposed in the housing;
   a sample cavity disposed in the housing, the sample cavity being fluidly coupled to the compressible reservoir through the passageway such that the tissue embedding material flows from the compressible reservoir, through the passageway, and into the sample cavity when the compressible reservoir is compressed or squeezed.

2. The tissue cassette assembly of claim 1, wherein the tissue embedding material comprises paraffin.

3. The tissue cassette assembly of claim 1, wherein the compressible reservoir is constructed from material selected from the group consisting of plastic, metal foil, polyester, fluorocarbon polymer, vinyl, and rubber.

4. The tissue cassette assembly of claim 1, wherein the compressible reservoir is permanently affixed to the tissue cassette assembly.

5. The tissue cassette assembly of claim 1, wherein the compressible reservoir is removable from the housing.

6. The tissue cassette assembly of claim 1, the passageway comprising a channel disposed within the housing.

7. The tissue cassette assembly of claim 1, the passageway comprising a tube embedded within the housing.

8. The tissue cassette assembly of claim 1, wherein the reservoir contains a volume of tissue embedding material capable of substantially filling the sample cavity.

9. The tissue cassette assembly of claim 1, the housing defining a first recess and a second recess, each recess containing a compressible reservoir.

10. A tissue cassette assembly, comprising:
    a housing;
    a compressible reservoir disposed in and attached to the housing, the compressible reservoir containing tissue embedding material; and
    a port disposed in the housing, the port in fluid communication with the compressible reservoir at one end and terminating in a sample cavity disposed in the housing at another end such that tissue embedding material flows from the compressible reservoir, through the port, and into the sample cavity when the compressible reservoir is compressed or squeezed.

11. The tissue cassette assembly of claim 10, further comprising a valve interposed between the compressible reservoir and the port.

12. The tissue cassette assembly of claim 10, wherein the compressible reservoir is constructed from material selected from the group consisting of plastic, metal foil, polyester, fluorocarbon polymer, vinyl, and rubber.

13. A tissue cassette assembly, comprising:
    a housing;
    a compressible reservoir disposed in and attached to the housing, the compressible reservoir containing a tissue embedding material;
    a moveable piston connected to the compressible reservoir, the moveable piston configured to apply pressure to the tissue embedding material in the compressible reservoir; and
    a port disposed in the housing, the port in fluid communication with the tissue embedding material in the compressible reservoir at one end and terminating in a sample cavity disposed in the housing at another end such that tissue embedding material flows from the compressible reservoir, through the port, and into the sample cavity when the movable piston applies pressure to the tissue embedding material in the compressible reservoir.

14. A reservoir for containing a tissue embedding material, comprising:
    a compressible container having an opening, the compressible container including a volume of tissue embedding material therein and being disposed in a housing of a tissue cassette assembly, the opening configured to fluidly couple with a port disposed in the housing, the port in fluid communication with a sample cavity disposed within the housing such that tissue embedding material flows from the compressible container through the opening, through the port, and into the sample cavity when the compressible reservoir is compressed or squeezed.

15. The tissue cassette assembly of claim 1, wherein the compressible reservoir is a pouch.

16. The tissue cassette assembly of claim 10, wherein the compressible reservoir is a pouch.

17. The tissue cassette assembly of claim 13, wherein the compressible reservoir is a pouch.

18. The tissue cassette assembly of claim 14, wherein the compressible container is a pouch.

19. The tissue cassette assembly of claim 1, wherein the compressible reservoir is disposed within a recess defined by the housing.

20. The tissue cassette assembly of claim 10, wherein the compressible reservoir is disposed within a recess defined by the housing.

21. The tissue cassette assembly of claim 13, wherein the compressible reservoir is disposed within a recess defined by the housing.

* * * * *

UNITED STATES PATENT AND TRADEMARK OFFICE
CERTIFICATE OF CORRECTION

PATENT NO. : 7,666,358 B2 Page 1 of 1
APPLICATION NO. : 11/551623
DATED : February 23, 2010
INVENTOR(S) : Steven A. Scampini It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 636 days.

Signed and Sealed this

Seventh Day of December, 2010

David J. Kappos
*Director of the United States Patent and Trademark Office*